United States Patent [19]

Goltry et al.

[11] Patent Number: 6,025,336
[45] Date of Patent: Feb. 15, 2000

[54] DETERMINING EXPOSURE TO IONIZING RADIATION AGENT WITH PERSISTENT BIOLOGICAL MARKERS

[75] Inventors: Kristin L. Goltry, Pittsburgh; Joel S. Greenberger, Sewickley, both of Pa.

[73] Assignee: University of Pittsburgh, Pittsburgh, Pa.

[21] Appl. No.: 08/602,145

[22] Filed: Feb. 15, 1996

[51] Int. Cl.[7] .............................. C12Q 1/68; C12Q 1/16; G01N 23/00; A01N 43/04

[52] U.S. Cl. .................................. 514/44; 435/1.1; 435/6; 435/7.1; 435/7.2; 435/35; 436/57; 436/58; 436/63; 436/64

[58] Field of Search .................................. 435/1.1, 6, 7.1, 435/7.2, 35, 968; 436/57, 58, 63, 64; 514/44

[56] References Cited

U.S. PATENT DOCUMENTS 5,346,814  9/1994  Hahn et al. ................................ 435/35

OTHER PUBLICATIONS

Drasin et al. "Pulmonary Hyalinizing Granulomas in a Patient with Malignant Lymphoma, with Development Nine Years Later of Multiple Myeloma and Systematic Amyloidosis" Cancer, vol. 44, pp. 215–220, Sep. 1979.

Martin et al. "Temporal Modulation of TGF– and –Actin Gene Expression in Pig Skin and Muscular Fibrosis after Ionizing Radiation" Radiation Research, vol. 34, pp. 63–70, 1993.

Goltry et al. "Indirect irradiation leukemogenesis through bone marrow stromal cells: use of differential . . . " Experimental Hematology, vol. 23, No. 8, p. 751, 1995.

Harris et al. "Use of mRNA differential display to identify changes in gene expression in HT29 human tumor . . . " Journal of Radiation Oncology Biology Physics, vol. 30, No. (suppl. 1) 1994.

Goltry et al. "Isolation of altered transcripts in irradiated bone marrow stromal cell line using differential . . . " Blood, vol. 86, No. (10 suppl. 1), 1995.

Kondratyev et "Detection of genes by ionizing radiation in human squamous carcinoma cells by differential display" Proc. Am. Assoc. Cancer Res. Ann. Met., vol. 35, No. 0, p. 639, 1994.

Goltry et al. "Changes in adhesion of a hematopoietic cell line to an irradiated bone marrow stromal cell line" Blood, vol. 86, No. (10 suppl. 1), 1995.

Greenberger et "Role of bone marrow stromal cells in irradiation leukemogenesis" Acta Haematologica, vol. 96, No. 1, pp. 1–15, 1996.

Liang et al., "Differential Display of Eukaryotic Messenger RNA by Means of the Polymerase Chain Reaction", Science, vol. 257, (1992) pp. 967–971.

Laing et al., "Distrib. & Cloning of Eukaryotic mRNAs by Means of Differential Display: Refinements and Optimization", Nucleic Acids Res., vol. 21, No. 14, (1993) pp. 3269–3275.

Steel et al., "The Major Acute Phase Reactants: C–Reactive Protein, Serum Amyloid P Component and Serum Amyloid A Protein", Immunology Today, vol. 15, No. 2, (1994) pp. 81–88.

Benditt et al., "Expression of the Third Member of the Serum Amyloid a Gene Family in Mouse Adipocytes", Journal Exp. Med., vol. 169, (1989) pp. 1841–1846.

Meek et al., "Amyloid A Gene Family Expression in Different Mouse Tissues", Journal Exp. Med., vol. 164, (1986) pp. 2006–2017.

Meek et al., "Mouse $SAA_3$: Detection in Mouse Tissue With Specific Antibody" Dept. of Pathology (SJ–60), University of Washington, (1991) pp. 75–78.

(List continued on next page.)

*Primary Examiner*—Ardin H. Marschel
*Assistant Examiner*—Jezia Riley
*Attorney, Agent, or Firm*—Foley & Lardner

[57] ABSTRACT

Persistent biological indicators of exposure to ionizing radiation, particularly nucleic acid indicators, can be employed in determining whether a subject has been exposed to ionizing radiation. Such biological indicators can be identified via the technique of differential display.

26 Claims, 3 Drawing Sheets

```
C122:   1   TGCTGACCTGCCTAAAAGATACTGAGTTTTCTCTTCCTGTTGTTCCCAGTC  51
            ||||  |||||||||||||||||||||||||||||||||||||||||||||
SAA3:   268 TGCTGGCCTGCCTAAAAGATACTGAGTTTTCTCTTCCTGTTGTTCCCAGTC  318

C122:   52  ATGCTGCCCCCCGAGAAGAGGAGCAACTACTGGGTTGAGATATTTTCTAAA  102
            |||||||||||||||||||||||||||||||||||||||||||||||||||
SAA3:   319 ATGCTGCCCCCCGAGAAGAGGAGCAACTACTGGGTTGAGATATTTTCTAAA  369

C122:   103 ATCTGGATCCCTAAACATCCCAATGTGCTGAATAAATACTTGTGAAATGCA  153
            |||||||||||||||||||||||||||||||||||||||||||||||||||
SAA3:   370 ATCTGGATCCCTAAACATCCCAATGTGCTGAATAAATACTTGTGAAATGCA  420
```

OTHER PUBLICATIONS

Greenberger, "Corticosteroid–Dependent Differentiation of Human Marrow Preadipocytes In Vitro", In Vitro, vol. 15, No. 10, (1979) pp. 823–828.

Greenberger, "Indirect Irradiation Leukemogenesis Through Bone Marrow Stromal Cells: . . . ", Experimental Hematology, vol. 23, No. 8, (1995) p. 751.

Goltry et al., "Use of Differential Display to Identify Genes With Altered Expression in an Irradiated Stromal Cell Line", Radiation Resh. Society North American Hyperthermia Soc. Abstract/Acceptance Form.

```
C122:    1 TGCTGACCTGCCTAAAAGATACTGAGTTTTCTCTTCCTGTGTTCCCAGTC  51
           ||||||| |||||||||||||||||||||||||||||||||||||||||
SAA3:  268 TGCTGGCCTGCCTAAAAGATACTGAGTTTTCTCTTCCTGTGTTCCCAGTC 318

C122:   52 ATGCTGCCCCCGAGAAGAGGAGCAACTACTGGGTTGAGATATTTTCTAAA 102
           |||||||||||||||||||||||||||||||||||||||||||||||||
SAA3:  319 ATGCTGCCCCCGAGAAGAGGAGCAACTACTGGGTTGAGATATTTTCTAAA 369

C122:  103 ATCTGGATCCCTAAACATCCCAATGTGCTGAATAAATACTTGTGAAATGCA 153
           |||||||||||||||||||||||||||||||||||||||||||||||||
SAA3:  370 ATCTGGATCCCTAAACATCCCAATGTGCTGAATAAATACTTGTGAAATGCA 420
```

FIGURE 1

```
C31:      11 TGAGATGTCCAG.AAGATGTTATTACCTGAAGAAGGGTGTGAAGGCTGAA   59
             ||||||||||||  |||||||||||||||||||||||||||||||||||
MSSP-1: 1175 TGAGATGTACAGAAAAGGTGTTCTTACATGAAGAAGGGTGTGAAGGCTGAA 1224

C31:      60 CAATCATGGATTTTTCTGATCAATTGTGCTTTAGGAAATTATTGACAGTT  109
             ||||||||||||||||||||||||||||||||||||||||||||||||||
MSSP-1: 1225 CAATCATGGATTTTTCTGATCAATTGTGCTTTAGGAAATTATTGACAGTT 1274

C31:     110 TTGCACAGGTTCTTGAAAACGTTATTTATAATGAAATCAACTAAAACTAT  159
             ||||||||||||||||||||||||||||||||||||||||||||||||||
MSSP-1: 1275 TTGCACAGGTTCTTGAAAACGTTATTTATAATGAAATCAACTAAAACTAT 1324

C31:     160 TTTTGCTATAAGTTCTATAAGGTGCATAAAACCCTTAAATTCATCTAGTA  209
             ||||||||||||||||||||||||||||||||||||||||||||||||||
MSSP-1: 1325 TTTTGCTATAAGTTCTATAAGGTGCATAAAACCCTTAAATTCATCTAGTA 1374

C31:     210 GCTGTTCCCCTGAACAGGTTTATTTTAGTAAAAAACAAAAAC          251
             |||||||| ||||||||||||||||||||||||||  |||||
MSSP-1: 1375 GCTGTTCCCCGAACAGGTTTATTTTAGTAAAAAAAAAAAAAC         1416
```

FIGURE 2A

| C31:    |   11 | TGAGATGTCCAG.AAGATGTTATTACCTGAAGAAGGGTGTGAAGGCTGGA |   59 |
| MSSP-2: | 1405 | TGAGATGTACAGAAAGGTGTTCTTACATGAAGAAGGGTGTGAAGGCTGAA | 1454 |
| C31:    |   60 | CAATCATGGATTTTCTGATCAATTGTGCTTTAGGAAATTATTGACAGTT |  109 |
| MSSP-2: | 1455 | CAATCATGGATTTTCTGATCAATTGTGCTTTAGGAAATTATTGACAGTT | 1504 |
| C31:    |  110 | TTGCACAGGTTCTTGAAAACGTTATTTATAATGAAATCAACTAAAACTAT |  159 |
| MSSP-2: | 1505 | TTGCACAGGTTCTTGAAAACGTTATTTGTGAAATCAACTAAAACTAT | 1554 |
| C31:    |  160 | TTTTGCTATAAGTTCTATAAGGTGCATAAAACCCTTAAATTCATCTAGTA |  209 |
| MSSP-2: | 1555 | TTTTGCTATAAGTTCTATAAGGTGCATAAAACCCTTAAATTCATCTAGTA | 1604 |
| C31:    |  210 | GCTGTTCCCCTGAACAGGTTTATTTTAGTAAAAAAAATCAAAGATTTTATCAAAT |  259 |
| MSSP-2: | 1605 | GCTGTTCCCCGAACAGGTTTATTTTAGTAAAA..........AA | 1639 |
| C31:    |  260 | AAAAAAAAAAAAAAAAAAAAAAAAAAAACGGAAAAAAAATCAAAGATTTTATCAAAT......... |  303 |
| MSSP-2: | 1640 | AAAAAAAGCAAAAAAC.....AAAAACAAAGATTTTATCAAATGTTATG | 1684 |
| C31:    |  304 | ATXXXAAAAAAAAAAAA |  319 |
| MSSP-2: | 1685 | ATGCAAAAAAAAAAAAA | 1700 |

FIGURE 2B

DETERMINING EXPOSURE TO IONIZING RADIATION AGENT WITH PERSISTENT BIOLOGICAL MARKERS

BACKGROUND OF THE INVENTION

The present invention relates to a method of determining whether a subject has been exposed to ionizing radiation, to a biological indicator, particularly a nucleic acid indicator, used in such a determination, and to a method of identifying biological indicators useful in detecting exposure to ionizing radiation.

The potential consequences of exposure to ionizing radiation make a biological indicator of past radiation exposure highly desirable. But conventional approaches in this regard have limited the available evidence of past exposure largely to gross pathology or circumstantial evidence, such as telangiectasia (new vessel) formation, fibrosis of skin or other organs, alopecia, cataract formation, sterilization, and teratogenesis (birth defects) in subjects in the first trimester of pregnancy at the time of exposure.

Molecular evidence of prior irradiation has been quite limited. For example, chromosome 2-specific deletions have been identified in hematopoietic cells of CBA/Ca mice that develop leukemia following exposure to an inducing dose of 200 cGy of ionizing radiation. The CBA/Ca mice develop a series of chromosomal abnormalities.

While specific chromosomal changes reproducibly have been demonstrated in hematopoietic cells, there has been no report that gamma irradiation exerts other detectable effects on the hematopoietic stem cells either directly or indirectly, for example, through effects on cells of the bone marrow stromal microenvironment.

Short-lived biochemical indicators also have been reported. For example, increased expression of mRNA for c-jun, c-fos and p53 has been observed in cell cultures following exposure to ionizing radiation. The increased expression is transient, with levels returning to normal as quickly as one hour after exposure. Similarly, elevated circulating levels of the protein TGF-β have been observed in patients exposed to at least 3000 cGy of x-rays in radiotherapy. In patients that do not develop pneumonitis, this level returns to normal by the end of radiotherapy, while in most patients developing pneumonitis, the elevated levels persisted by the end of therapy. In addition, expression of TGF-β varies from individual to individual.

Both the brevity of the TGF-β elevation and the variation in its expression from individual to individual renders the elevation unsuitable as an indicator of past exposure. Indeed, no biological indicator has been reported that is detectable weeks or months following exposure.

A persistent, detectable indicator of past exposure to ionizing radiation would be valuable both in basic radiation biology and in forensic pathology. The need is evident particularly in circumstances where a prior history of radiation exposure is not suspected or is questioned as the etiological agent of a given pathological condition.

SUMMARY OF THE INVENTION

It therefore is an object of the present invention to provide a biological indicator of exposure to ionizing radiation, which indicator is detectable weeks or months after exposure.

It is another object of the present invention to provide a method of identifying biological indicators of irradiation.

It is yet another object of the invention to provide a method of determining past exposure to ionizing radiation by detecting changes in the level of a biological indicator identified in accordance with the present invention.

In accomplishing these and other objects, there is provided, in accordance with one aspect of the present invention, a method of identifying a biological indicator of exposure to ionizing radiation, comprising the steps of exposing a population of cells to ionizing radiation; using differential display to compare gene expression in the population of cells exposed to the ionizing radiation to gene expression in a control population of cells not exposed to the ionizing radiation; and selecting a gene or gene fragment that has an altered level of gene expression in the exposed population of cells as compared to the control population of cells, which level of expression persists following exposure to the ionizing radiation.

The present invention further provides a method of determining whether an individual has been exposed to radiation, comprising the steps of obtaining cells from an individual and then assaying the cells for the presence of a persistent biological indicator of past exposure to radiation.

Also provided in accordance with the present invention is a kit for detecting past exposure to ionizing radiation, comprising primers specific for a gene or gene fragment that is a persistent indicator of past exposure to ionizing radiation; reagents for RT-PCR analysis; and instructions for using the primers and the reagents in an assay to determine whether cells removed from a subject contain the persistent indicator of past exposure to ionizing radiation.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. By way of example, it is apparent that biological indicators indicative of exposure to systemic toxins, to chemotherapeutic alkylating agents, to chemical carcinogens and to other agents which break DNA strands and induce irradiation repair can be identified in accordance with protocols set forth herein.

BRIEF DESCRIPTION OF THE DRAWINGS

FIG. 1 is a sequence comparison of band C122 (SEQ ID NO: 9), isolated from differential display gels, subcloned and sequenced as described herein, and the serum amyloid A3 gene (SEQ ID NO: 10).

FIGS. 2A and 2B are sequence comparisons of band C31 (SEQ ID NO: 11), isolated from differential display gels, subcloned and sequenced as described herein, and the MSSP-1 (SEQ ID NO: 12) and MSSP-2 (SEQ ID NO: 14) binding protein genes.

DETAILED DESCRIPTION OF PREFERRED EMBODIMENTS

A class of biological indicators has been discovered, particularly including nucleic acid indicators corresponding to genes or gene fragments, which is characterized by a persistence of weeks or months after exposure to ionizing radiation. In other words, the signal provided by the biological indicators of the present invention is distinctive of such exposure and persists for a significant period after exposure.

Putative biological indicators within the present invention are identified by determining changes in level of the biological indicator following in vitro exposure of a cell culture, particularly a bone marrow stromal cell culture (BMSCC), to ionizing radiation. The putative indicators are further evaluated to determine whether there is a corresponding change in the level the biological indicator following in vivo exposure of a subject to ionizing radiation. Those biological indicators that exhibit persistent, detectable in vivo changes in level following exposure of a subject to ionizing radiation are useful as biological indicators of past exposure to ionizing radiation.

A "persistent" change in the level of a biological indicator in accordance with the present invention is defined as a change that persists for at least 1 week following exposure to ionizing radiation. More particularly, it is a change that continues for at least three weeks following exposure, preferably for at least three months, and still more preferably for a year or longer after exposure.

A "detectable" change in the level of a biological indicator in accordance with the present invention is defined as a statistically significant change in the level of expression, compared to the level of expression of that biological indicator that naturally exists in a control population that has not been exposed to significant levels of ionizing radiation, i.e., that only has been exposed to levels of ionizing radiation that exist generally in the environment. A detectable change is defined more particularly as a level of expression that is at least double that found in the control population. Preferably, the level of the biological indicator in the control population is virtually undetectable by conventional techniques.

In a preferred embodiment, the biological indicator is a nucleic acid indicator that corresponds to a gene or gene fragment. These nucleic acid indicators are identified by using the technique of differential display to identify changes in gene expression at various timepoints after in vitro irradiation of a cell culture. Differential display is a powerful technique to compare gene expression between two or more RNA populations. See, for example, Liang and Pardee, *Science* 257: 967–71 (1992), and Liang et al., *Nucleic Acids Res.* 21: 3269–75 (1993), the respective contents of both of which are incorporated herein by reference. This technique allows the visualization of the total spectrum of differences, both induced and suppressed transcripts, between two or more populations of RNA simultaneously. Since the technique is PCR-based, the isolation of rare messages is possible. Differential display therefore provides advantages over traditional subtractive hybridization techniques.

In differential display, mRNAs are amplified by PCR and then distributed by their size on a denaturing polyacrylamide gel. A key element of the technique is the use of a set of oligonucleotide primers, one of which is anchored to the polyadenylate tail of a subset of mRNAs and the other of which is short and arbitrary and which anneals at different positions, relative to the first primer. The mRNA subpopulations defined by these primer pairs are amplified after reverse transcription and resolved on a denaturing polyacrylamide gel. Differential display allows not only the visualization of the total spectrum of differences between many populations of RNA simultaneously, but also the capacity to isolate and characterize these differences.

The technique of differential display reproducibly identifies genes or gene fragments that exhibit a change in level of expression following exposure to ionizing radiation. For example, according to the present invention, in vitro exposure of a murine bone marrow stromal cell line to ionizing radiation reproducibly produces numerous differential display fragments that correspond to either a detectable increase or decrease in the level of expression, as described below. Hence, putative murine biological indicators, the expression of which is stably increased or decreased by exposure to ionizing radiation, can be identified reproducibly in accordance with the present invention.

The technique of differential display similarly is applied to human cells to identify transcripts that correspond to either a detectable increase or decrease in level of expression following in vitro irradiation of a human cell line, in a protocol similar to that described herein for mice, and differential display can be used to identify those transcripts that are induced by the ionizing radiation. Alternatively, once a biological indicator has been identified in mice, primers specific for one or more homologous gene(s) in humans can be used to amplify the homologous human gene(s).

Particularly preferred as a biological indicator in accordance with the present invention is a gene of the serum amyloid A (SAA) family, a family of major acute phase inflammatory and oxidative stress genes produced by the liver during the systemic inflammatory response and produced locally by endothelial cells, fibroblasts, and macrophages in response to a variety of cytokines, including IL-1, IL-6 and TNF-α. Steel et al. *Immunol. Today* 15: 81–88 (1994). SAA is the precursor to amyloid A (AA) protein, a major component of amyloid fibrils deposited in tissues in the disease amyloidosis associated with chronic inflammation. A variety of stimuli, including tissue injury and inflammatory agents such as lipopolysaccharide (LPS), are effective in elevating SAA levels.

Members of the SAA family in mice include SAA1, SAA2, SAA3 and SAA4. The liver is the major site of SAA synthesis, but Northern blot analysis of extrahepatic tissues after LPS injection reveals distinct patterns of SAA1, SAA2, and SAA3 expression. SAA3 is the major extrahepatic SAA, and is detectable in lung, kidney, adrenal gland, intestine, heart, spleen, testis, skeletal muscle, stomach, brain, pituitary and pancreas. SAA3 induces the production of proteases and cell adhesion molecules and has been shown to induce directional migration and adhesion of hematopoietic cells. Steel et al., *Immunol. Today* 14(2): 797–809 (1986). The wide variety of tissues in which SAA3 is found means that a number of tissues, particularly skin and liver, may be assayed to determine past exposure to ionizing radiation.

The broad range of tissues that contain detectable levels of SAA3 after LPS injection further suggests that a single, dispersed cell system present in each of these tissues is responsible for SAA3 expression. In situ hybridization studies point to adipocytes as a primary source of extrahepatic SAA3 expression. See, for example, Benditt & Meek, *J. Exp. Med.* 169: 1841–46 (1989); Meek & Benditt, *J. Exp. Med.* 164: 2006–17 (1986); and Meek et al., "Mouse SAA3: Detection in Mouse Tissues with Specific Antibodies" in AMYLOID AND AMYLOIDOSIS (Kluwer, 1991). Thus, the assay of levels of SAA3 in adipocytes or pre-adipocytes particularly is indicated in determining past exposure to ionizing radiation.

The SAA3 gene in mice is induced four days after in vitro irradiation of BMSCCs, and message levels remain high at least three weeks after irradiation. The results show that exposure of cells to ionizing radiation in vitro induces the long-term production of the SAA3 message. A dose-response curve shows that message levels are detected after 100 cGy of ionizing radiation in vitro, and reach maximal induction after exposure to 500, 1,000 and 5,000 cGy.

While SAA3 is a preferred biological indicator according to the present invention, other differential-display fragments which show a persistent, detectable change in level following irradiation also are useful. Preliminary analysis of other of the differential display fragments that are identified following in vitro exposure of BMSCCs reveals that they arise from genes other than SAA3. These results implicate a series of genes characterized by detectable, persistent changes in level of expression after exposure to ionizing radiation.

Those genes that display an increase in level of expression following exposure to ionizing radiation are preferred, but it also is possible in principle to use genes that display a decrease in level of expression following exposure. Several differential-display transcripts that have decreased levels of expression following exposure to ionizing radiation are identified in accordance with the present invention. For example, a differential display fragment homologous to the gene encoding c-myc upstream single-stranded binding proteins, MSSP-1/MSSP-2, is described.

Expression of genes and gene fragments identified according to the invention by in vitro techniques is studied by comparing levels of those genes or gene fragments in BMSCCs established from subjects exposed to radiation, to BMSCCs established from control subjects. CBA/Ca mice, and substrains thereof, are suitable models for the study of in vivo expression. CBA/Ca mice develop myeloid leukemia after 200 cGy total body irradiation. BMSCCs are established from both CBA/Ca mice exposed to 200 cGy of ionizing radiation and from unexposed CBA/Ca mice.

In addition to measurable differences in the level of expression of genes identified by the in vitro analysis, quantifiable differences in patterns of establishment of permanent stromal cell lines and clonal sublines from BMSCCs from irradiated subjects as compared to BMSCCs from control subjects exist. Differences in the irradiation biology and hematopoietic support capacity of stromal cell lines established from irradiated subjects compared to control subjects also are observed for these cell lines. The data suggest in vivo irradiation-induced changes in the stromal cells of the hematopoietic microenvironment that persist for many months following explant to culture. These changes may combine with the irradiation-induced chromosomal changes in stem cells to influence leukemogenesis.

Bone marrow stromal cells are isolated from control mice and from mice exposed 100 days earlier to 200 cGy of ionizing radiation. The isolated cells are grown in vitro in BMSCCs for 3 months. Bone marrow stromal cell lines are established from both the control cultures and the cultures established from the previously irradiated mouse.

The cell lines thus obtained may be grown in culture for periods of several months or longer before the levels of SAA3 message are tested. A line derived from control cultures does not to contain significant levels of the SAA3 message until 1 week after exposure to 50 Gy ionizing radiation in vitro. These results are similar to those obtained from BMSCCs irradiated in vitro. In distinct contrast, a cell line established from a previously-irradiated mouse contains huge amounts of the SAA3 message. Irradiation of cells of this latter cell line in vitro increases SAA3 message levels even further: one week after exposure of this cell line to the 50 Gy ionizing radiation in vitro, the abundance of the SAA3 message increases 2–3 fold.

Thus, in vivo exposure of mice to ionizing radiation induces the SAA3 message in bone marrow stromal cells. An increased message level is detectable for up to one year after exposure. Detection of SAA3 levels in bone marrow stromal cells therefore is illustrative of detecting past irradiation in accordance with the present invention. While the examples herein report increased expression in bone marrow stromal cells, other cells, including lung, spleen, kidney, liver, heart, thymus, and brain, be used as target cells for detection of increased levels of SAA3 following exposure. As noted above, adipocytes and pre-adipocytes are particularly favored as cells for detection of increased levels of SAA message.

In vivo expression is studied by collecting whole bone marrow and other tissues from control and previously-irradiated mice at various timepoints and immediately isolating the RNA. Total RNA is analyzed for expression of transcripts identified in vitro as having altered levels of expressions. Transcripts that display altered levels following in vitro irradiation similarly are found to display persistently altered levels of in vivo expression. For example, no message for SAA3 is detected in control samples, but SAA3 message is detected at extended times following the in vivo exposure.

Results similar to those in mice are observed in humans. The human SAA gene family comprises at least four members. Human cell lines, preferably, bone marrow stromal cell lines, are exposed to ionizing radiation in vitro, in a protocol similar to that described herein for mice, and differential display is used to identify those members of the SAA gene family that are induced by the ionizing radiation. In vivo expression of SAA genes can be confirmed in patients exposed to ionizing radiation during treatment for leukemia, lymphoma, multiple myeloma or solid tumors including breast cancer where autologous bone marrow transplantation is planned. Specific primers generated for each family member, and reverse transcriptase (RT) PCR amplification of each SAA gene in the family with these primers is used in determining the gene or genes within the human SAA gene family that are induced. Of particular interest are the human genes SAA1 and SAA2. The human SAA2 gene behaves like the mouse SAA3 gene, that is, it is virtually undetectable in controls but displays a persistent, detectable increase following exposure to ionizing radiation. The human SAA1 gene is present in both control and irradiated cultures.

Once a biological indicator in accordance with the present invention is identified, it can be used to determine whether a subject previously has been exposed to ionizing radiation. An assay is used to measure the level of expression of the biological indicator in a population of cells that may have been exposed to ionizing radiation. This level is compared to the level of expression in a control population that has not been exposed to significant levels of ionizing radiation. The cells to be assayed may be either cells recently removed from a subject or cells previously removed from a subject and then cultured. The assay employs either Northern blot or RT-PCR techniques. When RT-PCR is used to detect past exposure, sequences specific to irradiation-induced transcripts identified by differential display analysis in accordance with the invention are used as primers.

The components for determining whether a subject previously has been exposed to ionizing radiation are conveniently packaged together in kit for detecting past exposure to ionizing radiation. The kit includes primers specific for a gene or gene fragment that is a persistent indicator of past exposure to ionizing radiation, reagents for RT-PCR analysis, and instructions for using the primers and the reagents in an assay to determine whether cells removed from a subject contain the persistent indicator of past exposure to ionizing radiation. In a preferred embodiment, the kit includes primers specific for a SAA gene, particularly human SAA1 or human SAA2.

The following examples illustrate a specific protocol for identifying persistent, detectable biological indicators that are symptomatic of past exposure to ionizing radiation. It will be appreciated that various changes and modifications to the described protocol can be made within the spirit and scope of the invention.

EXAMPLE 1

In vitro irradiation of murine cells and isolation of RNA

A variety of murine cell lines have been exposed to in vitro ionizing radiation according to the present invention. Primary among these is the D2XRII cell line, a murine fibroblastic stromal cell line, originally isolated from C3H/HeJ long-term bone marrow cultures, which has been described previously. These cells have been classified as bone marrow fibroblasts or pre-adipocytes. Naparstek et al., *J. Cell Physiol.* 126:407 (1986). D2XRII cells were grown to confluent monolayers in DMEM containing 10% FBS and then exposed to 1, 5, 10 or 50 Gy of 6 MeV X-rays at a dose rate of 200 cGy/min. Cells were harvested 1 hour, 1 day, 4 days, 1 week, 2 weeks, and 3 weeks after irradiation. Total RNA was isolated using a Total RNA Isolation Kit (Promega Corp., Madison, Wis.), based on the method of Chomcynski and Sacchi, *Anal. Biochem.* 162: 156 (1987). DNase-treated total RNA was used in Northern blot, RT-PCR, and differential display analysis.

EXAMPLE 2

Differential display analysis

The differential display protocol uses commercially-available RNAmap kits (GenHunter Corp., Brookline, Mass.). Briefly, 200 ng of DNase-treated total RNA was used as a template for reverse transcription using one of four oligo (dT)-based primers. After reverse transcription, the cDNA was PCR amplified with a combination of the oligo (dT) primer and one of 20 arbitrary 10-base primers. Amplification of the cDNA with the combination of 4 downstream oligo (dT)-based primers and 20 upstream arbitrary primers displayed 10,000 of the mRNA species present in a cell (Liang et al., 1993). After amplification, the PCR products were separated on a 6% denaturing polyacrylamide gel. The gel then was dried, and the products were detected by autoradiography.

The abundance of each display transcript was then compared between RNA populations. To minimize the isolation of false positives, each differential display reaction was performed twice from the same population of RNA and only transcripts exhibiting the same altered abundance in both sets of reactions were examined further.

Bands that showed differential expression were cut directly from the polyacrylamide gel. DNA was isolated from the gel slice, PCR amplified with Taq DNA polymerase using the original primers and conditions, and ligated into the pT7-Blue T-vector. The resulting plasmid was used to transform XL-1 Blue cells (Novagen Inc., Madison, Wis.). Colonies containing cloned PCR products were isolated, and the insert sequenced from plasmid using an fmol DNA sequencing kit (Promega Corp., Madison, Wis.). In situations where more than one sequence was obtained from the subcloned fragment, each sequence was verified for its expression pattern to determine which was the sequence of interest.

EXAMPLE 3

Northern blot analysis

Northern blots were performed as described, for example, by Sambrook et al., MOLECULAR CLONING: A LABORATORY MANUAL (Cold Spring Harbor Laboratory Press, 1989), the contents of which are incorporated herein by reference. Briefly, 10–20 µg of total RNA was electrophoresed on a 1% formaldehyde-agarose gel, transferred to a supported nitrocellulose membrane (Schleicher and Schuell) and hybridized with a $\alpha^{32}$P-dCTP (NEN)-label probe representing the PCR subclone of interest in a solution containing 1% BSA, 250 mM $Na_2HPO_4$, 1 mM EDTA, and 7% SDS. After washing, the blot was exposed to X-omat film (Kodak) and the bands were quantitated by densitometry. The same blot was stripped using boiling 0.1% SDS and hybridized sequentially with a probe representing the glyceraldehyde-3-phosphate dehydrogenase gene (G-3-PDH) as a loading control for the amount of RNA in each lane.

EXAMPLE 4

RT-PCR analysis

Oligo (dT)-primed reverse transcription of DNase-treated RNA (1 µg) was performed in a total volume of 20 µl in 20 mM Tris-HCl pH 8.4, 50 mM KCl, 5 mM $MgCl_2$, 1 mM dNTP, 20 Units RNase Inhibitor (Pharmacia, Piscataway, N.J.) with 200 Units reverse transcriptase (Gibco-BRL, Gaithersburg, Md.). The reaction was incubated at room temperature for 10 minutes, then at 37° C. for 45 minutes. This was followed by a 5-minute denaturation at 99° C. A control reaction was performed in the absence of reverse transcriptase. The reactions were diluted to 100 µl with water and 5 µl (approximately 50 ng of input RNA) was amplified with 20 pmol of sense primer and 20 pmol of antisense primer in the presence of 200 µM dNTP, 1.5 mM $Mgcl_2$, Tris-HCl pH 8.4, and 2.5 Units of Taq DNA polymerase (Boehringer Nannheim) for 20 cycles of 30 seconds at 94° C., 30 seconds at 60° C., and 1 minute at 72° C. Parallel PCR reactions with primers specific to the subclone or gene of interest and primers for the G-3-PDH gene were performed. After amplification, products were electrophoresed on an agarose gel and visualized by ethidium bromide staining.

EXAMPLE 5

Analysis of differential display transcripts obtained following in vitro irradiation of murine cells In vitro irradiation of D2XRII cells in culture produced a group of differential display transcripts representing either an increase or decrease in level of expression of a gene. A first group of 24 clones, in which expression was increased, are listed in Table 1.

TABLE 1

Molecular Clones with Increased Expression Isolated from Differential Display Gels of Irradiated D2XRII Bone Marrow Stromal Cells

| | Time: | | | | | | | |
|---|---|---|---|---|---|---|---|---|
| | 1 H | 1 H | 1 H | 1 D | 1 D | 1 W | 1 W | |
| | | | Dose (Gy): | | | | | Size |
| Clone | 0 | 10 | 50 | 10 | 50 | 10 | 50 | (bp) |
| C21 | (+) | – | – | + | + | + | + | 353 |
| G91 | – | – | – | – | – | 2+ | 2+ | 195 |
| G101 | (+) | + | + | + | + | 2+ | 2+ | 268 |
| A12 | (+) | (+) | (+) | (+) | (+) | 2+ | + | 475 |
| A113 | – | – | – | (+) | (+) | + | + | 430 |
| T34 | + | + | + | + | + | 2+ | 2+ | 270 |
| T36 | (+) | (+) | (+) | (+) | (+) | + | + | 255 |
| T101/2 | – | – | – | – | – | + | + | 345 |
| C122 | (+) | (+) | (+) | (+) | (+) | 3+ | 3+ | 185 |
| G63 | (+) | (+) | (+) | 2+ | 2+ | 2+ | 2+ | 250 |
| G143 | – | + | + | + | + | + | + | 265 |
| A41 | – | – | – | + | + | + | + | >600 |
| A63 | + | + | + | 2+ | 2+ | 3+ | 2+ | 325 |
| A91 | – | – | – | + | + | + | + | 550 |
| A92 | – | – | – | + | + | + | + | 340 |
| A111 | – | – | – | + | + | + | + | >600 |
| A112 | (+) | (+) | (+) | + | + | + | + | 475 |
| A181 | – | – | – | + | + | + | + | 600 |
| T61 | – | + | + | + | + | + | + | 320 |
| C51 | – | – | – | + | + | + | + | 265 |
| C54 | – | + | + | 2+ | 2+ | 2+ | 2+ | 470 |
| C91 | + | + | + | 2+ | 2+ | 2+ | 2+ | 362 |
| C102 | – | (+) | (+) | + | + | + | + | 520 |
| C103 | – | – | – | 2+ | 2+ | 2+ | 2+ | 340 |

This table shows all reproducibly differentially expressed bands identified from 80 combinations of primers used in differential display reactions (done in duplicate).
These clones have demonstrated altered expression with both time after exposure (1 hour (1 H), 1 day (1 D), and 1 week (1 W)) and dose (10 Gy (10) or 50 Gy (50)) of ionizing radiation.
Each band is listed with its expression pattern (absent (–); present (+)) and size.

Seven of these differential display transcripts, G91, G101, A113, T34, T36, T101/2 and C122 (SEQ ID NO: 9), exhibited a level that increased at the one week mark after irradiation, and these were selected for further study. One of these seven transcripts, clone C122 (SEQ ID NO: 9), was reamplified, subcloned and sequenced.

The differential expressed sequence was used to search the GenBank database to determine the existence of homology with known sequences. The comparison revealed C122 (SEQ ID NO: 9) to be identical to the 3' end of the murine serum amyloid A3 gene (SEQ ID NO: 10). The comparison is shown in FIG. 1. Bestfit comparison with sequences in GenBank show 99% identity to the SAA3 gene.

In cases where no homology of a selected fragment with a reported sequence is found, the PCR product of the unknown sequence can be used as a probe to screen the appropriate cDNA library (control or irradiated) for the full-length clone. See Sambrook et al. (1989), supra.

A second group of 12 clones, in which expression was decreased, are listed in Table 2.

TABLE 2

Molecular Clones with Decreased Expression Isolated from Differential Display Gels of Irradiated D2XRII Bone Marrow Stromal Cells

| | Time: | | | | | | | |
|---|---|---|---|---|---|---|---|---|
| | 1 H | 1 H | 1 H | 1 D | 1 D | 1 W | 1 W | |
| | | | Dose (Gy): | | | | | Size |
| Clone | 0 | 10 | 50 | 10 | 50 | 10 | 50 | (bp) |
| C31 | + | 2+ | 2+ | – | – | – | – | 347 |
| C84 | + | + | + | – | – | – | – | 462 |
| G32 | 3+ | 3+ | 3+ | + | + | + | + | 275 |
| G82 | + | + | + | – | – | – | – | 220 |
| G111 | + | + | + | – | – | – | – | 600 |
| G141 | 2+ | 2+ | 2+ | – | – | – | – | 385 |
| G142 | + | + | + | – | – | – | – | 290 |
| G152 | + | + | + | – | – | – | – | 208 |
| A121 | + | + | + | – | – | – | – | 410 |
| T11 | + | + | + | + | + | – | – | 195 |
| T62 | 2+ | 2+ | 2+ | + | + | – | – | 305 |
| T111 | 3+ | 3+ | 3+ | + | + | – | – | 425 |

This table shows all reproducibly differentially expressed bands identified from 80 combinations of primers used in differential display reactions (done in duplicate).
These clones have demonstrated altered expression with both time after exposure (1 hour (1 H), 1 day (1 D), and 1 week (1 W)) and dose (10 Gy (10) or 50 Gy (50)) of ionizing radiation.
Each band is listed with its expression pattern (absent (–); present (+)) and size.

Of the clones exhibiting a decrease in expression, clone 31 was found to be homologous to c-myc upstream single-stranded binding proteins, MSSP-1 (SEQ ID NO: 12) and MSSP-2 (SEQ ID NO: 14). The comparisons are shown in FIGS. 2A and 2B, respectively. Bestfit comparison with sequences in GenBank show 95% identity to both the MSSP-1 (SEQ ID NO: 12) and MSSP-2 (SEQ ID NO: 14) genes.

Increased expression of SAA3 has been demonstrated in other cell lines following in vitro exposure to radiation. For example, a two-fold increase in level of the SAA3 message has been found following exposure of a macrophage cell line.

EXAMPLE 6

Northern blot verification of expression of SAA3 by in vitro-irradiated cells

Expression of SAA3 by clone C122 (SEQ ID NO: 9) was verified by Northern blot analysis. RNA was collected from D2XRII cells 1 hour, 1 day, 1 week or 3 weeks after exposure of cells to 10 or 50 Gy of X-rays. After electrophoresis on a 1% formaldehyde-agarose gel, RNA was transferred to nitrocellulose and hybridized with a $^{32}$P-labelled probe representing the differential display band C122 (SEQ ID NO: 9). Hybridization signals were detected by autoradiography. Ethidium bromide staining of the agarose gel verified the presence of RNA in each lane. The Northern blot analysis confirms that differential display fragments identified in irradiated cells are not artifacts.

EXAMPLE 7

Expression of SAA3 versus time following in vitro exposure of murine cells and formulation of a dose-response curve Expression of SAA3 by clone C122 (SEQ ID NO: 9) at times longer than one week following irradiation also was verified by Northern blot analysis. RNA was collected from D2XRII cells 1 hour, 1 day, 4 days or 1 week, 2 weeks or 3 weeks after exposure to 10 Gy of x-rays. After electrophoresis on a 1% formaldehyde-agarose gel, RNA was transferred to nitrocellulose and hybridized with a $^{32}$P-labelled probe representing the differential display band C122. Hybridization signals were detected by autoradiography. Ethidium bromide staining of the agarose gel verified the presence of RNA in each lane.

The SAA3 gene was induced 4 days after in vitro irradiation, and message levels remained high at least 3 weeks after irradiation. Following exposure to 10 Gy of x-rays, the abundance of the SAA3 transcript was increased approximately 10-fold at 4 days post exposure, 20-fold at one week post exposure, 35-fold at two weeks post exposure and 40-fold at three weeks post exposure. This indicates that exposure of cells to ionizing radiation in vitro induced the long-term production of the SAA3 message. A dose-response curve for SAA3 shows that message levels are detected after 100 cGy of ionizing radiation in vitro, and reach maximal induction after exposure to 500, 1,000 and 5,000 cGy.

EXAMPLE 8

Expression of SAA3 in cell cultures established from mice exposed to ionizing radiation CBA/Ca male mice (Brookhaven Laboratories, N.Y.) received 200 cGy total body irradiation (250 KVP, GE Maxitron, dose rate 90 R/min, 1 mm aluminum and 0.5 mm copper filtration). Irradiated mice were sacrificed by cervical dislocation at 100 days after irradiation. A control group comprised an equal number of age-matched male CBA/Ca control mice.

Bone marrow from irradiated and control mice, respectively, was flushed into conical 15 ml centrifuge tubes in Fisher's medium supplemented with 25% horse serum and $10^{-5}$M hydrocortisone. Continuous bone marrow cultures were established individually from the hind limbs (tibia and fibula) of irradiated and control mice, respectively.

After week 4, 25% fetal calf serum was substituted for horse serum, according to published methods, to maximize longevity of the cultures. The cultures were maintained until they no longer demonstrated detectable cobblestone islands or production of over 10$^4$ cells/flask at weekly medium change. Representative flasks were sacrificed to establish bone marrow stromal cell lines at specified timepoints. Isolated cells were grown in vitro for 3 months.

Bone marrow stromal cell lines were established both from cultures of bone marrow stromal cells from control mice and cultures of bone marrow stromal cells from previously irradiated mice. The cell lines thus obtained were grown in culture for approximately one year before the levels of message for a putative biological indicator identified by an in vitro technique according to the invention were tested. Levels of the putative biological indicator are assessed using the same techniques described herein for D2XRII cells exposed to ionizing radiation in vitro.

Specific primers for members of the SAA murine gene family, shown in Table 3, were used to amplify murine SAA1, SAA2, SAA3 and SAA4 genes in the cultures from control and irradiated mice. None of the SAA transcripts were identified in control cultures, but SAA3 transcript was found in cultures from irradiated mice.

TABLE 3

Primer sequences for murine SAA family members

| Transcript | Primer Sequence | Product Size (bp) |
|---|---|---|
| muSAA1 | GAAGGAAGCTAACTGGAAAAACTC CAGGCCCCCAGCACAACCTACT (SEQ ID NO: 1) | 284 |
| muSAA2 | ATGAAGGAAGCTGGCTGGAAAGATG CTCAGGACCCCAACACAGCCTTCT (SEQ ID NO: 2) | 268 |
| muSAA3 | AGCCTTCCATTGCCATCATTCTT ACCCAGTAGTTGCTCCTCTTCTCG (SEQ ID NO: 3) | 426 |
| muSAA4 | GCTTGGGGAAGGAAGAC ACCTAATATGTGTCATCTAATAAGT (SEQ ID NO: 4) | 345 |

A representative line derived from control cultures, designated the CC3 cell line, was found not to contain significant levels of the SAA3 message until 1 week after exposure to 50 Gy ionizing radiation in vitro. One week after exposure of this cell line to the 50 Gy ionizing radiation in vitro, the abundance of the SAA3 message increased 2- to 3-fold. This result parallels that obtained for in vitro irradiation of D2XRII cells.

By contrast, a representative cell line established from a previously-irradiated mouse, designated the CT4 cell line, was found to contain huge amounts of the SAA3 message. Irradiation of cells from the CC4 cell line in vitro increased SAA3 message levels even further.

Expression of SAA3 in CC3 and CT4 cells was verified by Northern blot analysis. RNA was collected from the cells 1 week after exposure to 0 or 50 Gy of x-rays. The blots were hybridized with a $^{32}$P-labelled probe representing the differential display band C122 (SEQ ID NO: 9). Hybridization signals were detected by autoradiography. Ethidium bromide staining of the agarose gel verified equal loading of RNA in each lane.

EXAMPLE 10

In vivo expression of SAA3 in mice exposed to ionizing radiation

CBA/CaJ (Jackson Laboratories, Bar Harbour, Me.) mice, a substrain of CBA/Ca mice, were used to confirm increased expression of SAA3 following in vivo exposure to ionizing radiation. CBA/CaJ mice were exposed to 50 cGy, 200 cGy, 400 cGy and 700 cGy total body irradiation x-rays. Mice were sacrificed at 7 days, 14 days, 28 days, 3 months and 7 months following exposure, and whole bone marrow and other tissues were collected. RNA was isolated from the bone marrow and tissues and immediately analyzed for presence of SAA1, SAA2, SAA3 and SAA4 message, using RT-PCR with primers specific for each of SAA1, SAA2, SAA3 and SAA4, as described in Example 8. No message was detected in control marrow, but in mice exposed to 700 cGy total body irradiation SAA3 message was detected in marrow at extended timepoints following exposure.

Similar results have been obtained with cells from other strains of mice, including C57B16/J and C3H/HeJ mice. The results show that the in vivo exposure of mice to ionizing radiation induced the SAA3 message in bone marrow stromal cells, and this increase in message level was still detectable long after exposure. This shows that the SAA3 gene is suitable as a biological indicator of exposure to ionizing radiation.

EXAMPLE 9

Expression of SAA transcripts following in vitro irradiation of human cells

A variety of human cell lines were exposed in vitro to ionizing radiation according to the present invention. Primary among these are bone marrow stromal cell lines KM101, KM102 and KM104, which are described in FitzGerald et al., *Int. J. Rad. Oncol. Biol. Phys.* 15:1153–1159 (1988). The cells were grown to confluent monolayers in DMEM containing 10% FBS and then exposed to either 0 Gy (control) or 10 Gy of ionizing radiation. Specific primers for members of the SAA human gene family, shown in Table 4, were used to amplify human SAA1, SAA2, SAA3 and SAA4 genes.

TABLE 4

Primer sequences for human SAA family members

| Transcript | Primer Sequences | Product Size (bp) |
| --- | --- | --- |
| huSAA1 | CTCGGGACATGTGGAGAGCCTACTC TATTAGATACCCATTGTGTACCCTCT (SEQ ID NO: 5) | 369 |
| huSAA2 | CTCGGGACATGTGGAGAGCCTACTC TGCCATATCTCAGCTTCTCTGGACATA (SEQ ID NO: 6) | 376 |
| huSAA3 | GAGATGGGGTCTTGCTATGTTTC TAGGGATATAGAATTCAAGTAACTGTAGGT (SEQ ID NO: 7) | 491 |
| huSAA4 | AAGATACCAGCAGCTCTGCCTTTAC ACTTCGAGTCCTCCAATACAGTGC (SEQ ID NO: 8) | 368 |

In all three cell lines, the SAA1 transcript was observed in irradiated cells. The message level was increased in the irradiated cells as compared to the control cells. A SAA1 transcript was observed in control KM101 cells beginning at day 4. A SAA2 transcript was not observed in any control cells at any time, but was observed in irradiated cells, and persists following exposure. SAA3 and SAA4 transcripts were not detected in either control or irradiated cells.

EXAMPLE 10

Expression of SAA transcripts following in vivo exposure of humans to ionizing radiation To confirm expression of SAA transcripts in humans, samples from patients are taken before exposure of ionizing radiation during treatment for leukemia, lymphoma, multiple myeloma or solid tumors including breast cancer where autologous bone marrow transplantation is planned. The samples are cryopreserved. The patients then receive total body irradiation, and when evidence of clinical recurrence, or at specific timepoints following irradiation, bone marrow is aspirated for analysis and grown in tissue culture. Techniques for obtaining and expanding human bone marrow stromal cells are described in Greenberger, *In Vitro*, 15(10):823–828 (1979), the contents of which are incorporated herein by reference.

After removal of part of the sample for histopathological analysis for clinical purposed, the aspirated bone marrow is placed in tissue culture flask in 25% fetal calf serum supplemented with $10^{-6}M$ hydrocortisone and McCoys 5A medium. The cells are grown at 33° C. in a high humidity incubator and 7% $CO_2$. The stromal cells attached to the flask surface are expanded by trypsinization and replating.

An aliquot of bone marrow cells cryopreserved from the same patient prior to treatment with ionizing radiation is thawed and the cells are cultured under the same conditions. Stromal cells growing as attached monolayers on the flack surface in the presence of 25% fetal calf serum and $10^{-6}M$ hydrocortisone are expanded. After cells grow to an appropriate number, approximately $10^7$ cells in each preparation, they are harvested by scraping or trypsinization. Total RNA is extracted and amplified by RT-PCR, using human SAA transcripts, and the level of each SAA transcript is assayed and confirmed by Northern blot, as described above.

EXAMPLE 11

Assay for determining past exposure to ionizing radiation in a human subject Bone marrow stromal cells are biopsied from a human subject in order to detect whether that subject exhibits increased expression of SAA relative to that in a control population that has not been exposed to significant levels of ionizing radiation. The cells may be immediately assayed for level of the SAA, using the protocol and primers described above in Example 9, or they may be cultured following removal from the subject and subsequently assayed for level of SAA.

The protocols set forth above can be used to identify biological indicators for exposure to causative agents other than prior irradiation, for example, exposure to systemic toxins, to chemotherapeutic alkylating agents, to chemical carcinogens and to other agents which break DNA strands and induce irradiation repair. More particularly, differential display can be used to detect increased levels of expression of biological indicators in accordance with the present invention in tissues taken from subjects that have been exposed to the causative agent.

What is claimed is:

1. A method of identifying a biological indicator of exposure to ionizing radiation, comprising the steps of:
   exposing a population of cells to ionizing radiation;
   using differential display to compare gene expression in the population of cells exposed to the ionizing radiation to gene expression in a control population of cells not exposed to the ionizing radiation; and
   selecting a serum amyloid gene or serum amyloid gene fragment that has an altered level of gene expression in the exposed population of cells as compared to the control population of cells, which level of expression persists for at least three weeks following exposure to the ionizing radiation.

2. A method according to claim 1, additionally comprising a step of sequencing the gene or gene fragment.

3. A method according to claim 1, wherein the step of exposing a population of cells to ionizing radiation is a step of exposing a culture of cells in vitro.

4. A method according to claim 1, wherein the step of exposing a population of cells to ionizing radiation is a step of exposing cells in vivo.

5. A method according to claim 1, wherein the serum amyloid is murine serum amyloid A3.

6. A method according to claim 1, wherein the serum amyloid is human serum amyloid A1 or A2.

7. A method according to claim 1, wherein the cells are bone marrow cells.

8. A method according to claim 1, wherein the gene or gene fragment has a level of gene expression in the exposed population of cells that is increased as compared to the control population of cells.

9. A method according to claim 8, wherein the increased level of expression is at least double that found in the control population.

10. A method according to claim 8, wherein the level of the biological indicator in the control population is virtually undetectable by conventional techniques.

11. A method of determining whether an individual has been exposed to radiation, comprising the steps of obtaining cells from an individual and then assaying the cells for the presence of a gene or gene fragment that corresponds to a gene that encodes a serum amyloid that persists for at least three weeks following exposure to radiation.

12. A method according to claim 11, additionally comprising a step of culturing the cells prior to the step of assaying the cells.

13. A method according claim 11, wherein Northern blot analysis is used in the assaying step.

14. A method according claim 11, wherein RT-PCR analysis is used in the assaying step.

15. A method according to claim 11, wherein the biological marker is a gene or gene fragment corresponds to a gene that encodes a serum amyloid.

16. A method according to claim 11, wherein the serum amyloid is murine serum amyloid A3.

17. A method according to claim 11, wherein the serum amyloid is human serum amyloid A1 or A2.

18. A method according to claim 11, wherein the cells are bone marrow cells.

19. A method according to claim 11, wherein the gene or gene fragment has a level of gene expression in the exposed population of cells that is increased as compared to the control population of cells.

20. A method according to claim 19, wherein the increased level of expression is at least double that found in the control population.

21. A method according to claim 19, wherein the level of the biological indicator in the control population is virtually undetectable by conventional techniques.

22. A kit for detecting past exposure to ionizing radiation, comprising:
   primers specific for a serum amyloid gene or serum amyloid gene fragment that changes its level of expression in response to exposure to ionizing radiation, which level of expression persists for at least three weeks following the exposure to the ionizing radiation;
   reagents for RT-PCR analysis; and
   instructions for using the primers and the reagents in an assay to determine whether cells removed from a subject have an altered level of expression of the gene or gene fragment as compared to expression in cells in a control population.

23. A kit as claimed in claim 22, wherein the cells are bone marrow cells.

24. A kit as claimed in claim 23, wherein the primers are specific to a serum amyloid A gene or fragment thereof.

25. A method according to claim 11, wherein the biological indicator is one that persists for at least three months following exposure to radiation.

26. A method according to claim 11, wherein the biological indicator is one that persists for at least one year following exposure to radiation.

* * * * *

UNITED STATES PATENT AND TRADEMARK OFFICE
CERTIFICATE OF CORRECTION

PATENT NO. : 6,025,336
DATED : February 15, 2000
INVENTOR(S) : Kristin L. Goltry and Joel S. Greenberger It is certified that error appears in the above-identified patent and that said Letters Patent is hereby corrected as shown below:

Column 1,
Line 4, after the title insert:
-- The Invention disclosed herein was made with Government support under NIH Grant No. CA39851-12 from the National Institutes of Health. Accordingly, the U.S. Government has certain rights in this invention. --.

Signed and Sealed this

Seventh Day of February, 2006

JON W. DUDAS
*Director of the United States Patent and Trademark Office*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 46 base pairs
      (B) TYPE: nucleic acid (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:1:

GAAGGAAGCT AACTGGAAAA ACTCCAGGCC CCCAGCACAA CCTACT        46

(2) INFORMATION FOR SEQ ID NO:2:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:2:

ATGAAGGAAG CTGGCTGGAA AGATGCTCAG GACCCCAACA CAGCCTTCT        49

(2) INFORMATION FOR SEQ ID NO:3:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

AGCCTTCCAT TGCCATCATT CTTACCCAGT AGTTGCTCCT CTTCTCG        47

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

GCTTGGGGAA GGAAGACACC TAATATGTGT CATCTAATAA GT        42

(2) INFORMATION FOR SEQ ID NO:5:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

CTCGGGACAT GTGGAGAGCC TACTCTATTA GATACCCATT GTGTACCCTC T        51

(2) INFORMATION FOR SEQ ID NO:6:

(i) SEQUENCE CHARACTERISTICS:
        (A) LENGTH: 52 base pairs

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:6:

CTCGGGACAT GTGGAGAGCC TACTCTGCCA TATCTCAGCT TCTCTGGACA TA          52

(2) INFORMATION FOR SEQ ID NO:7:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:7:

GAGATGGGGT CTTGCTATGT TTCTAGGGAT ATAGAATTCA AGTAACTGTA GGT          53

(2) INFORMATION FOR SEQ ID NO:8:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:8:

AAGATACCAG CAGCTCTGCC TTTACACTTC GAGTCCTCCA ATACAGTGC              49

(2) INFORMATION FOR SEQ ID NO:9:

(i) SEQUENCE CHARACTERISTICS:
            (A) LENGTH: 153 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TGCTGACCTG CCTAAAAGAT ACTGAGTTTT CTCTTCCTGT TGTTCCCAGT CATGCTGCCC   60

CCCGAGAAGA GGAGCAACTA CTGGGTTGAG ATATTTTCTA AAATCTGGAT CCCTAAACAT  120

CCCAATGTGC TGAATAAATA CTTGTGAAAT GCA                              153

(2) INFORMATION FOR SEQ ID NO:10:

(i) SEQUENCE CHARACTERISTICS:
            (A) LENGTH: 153 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

TGCTGGCCTG CCTAAAAGAT ACTGAGTTTT CTCTTCCTGT TGTTCCCAGT CATGCTGCCC   60

CCCGAGAAGA GGAGCAACTA CTGGGTTGAG ATATTTTCTA AAATCTGGAT CCCTAAACAT  120
```

```
CCCAATGTGC TGAATAAATA CTTGTGAAAT GCA                                 153

(2) INFORMATION FOR SEQ ID NO:11:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TGAGATGTCC AGAAGATGTT ATTACCTGAA GAAGGGTGTG AAGGCTGAAC AATCATGGAT      60

TTTTCTGATC AATTGTGCTT TAGGAAATTA TTGACAGTTT TGCACAGGTT CTTGAAAACG     120

TTATTTATAA TGAAATCAAC TAAAACTATT TTTGCTATAA GTTCTATAAG GTGCATAAAA     180

CCCTTAAATT CATCTAGTAG CTGTTCCCCT GAACAGGTTT ATTTTAGTAA AAACAAAAA      240

C                                                                    241

(2) INFORMATION FOR SEQ ID NO:12:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TGAGATGTAC AGAAAGGTGT TCTTACATGA AGAAGGGTGT GAAGGCTGAA CAATCATGGA      60

TTTTTCTGAT CAATTGTGCT TTAGGAAATT ATTGACAGTT TTGCACAGGT TCTTGAAAAC     120

GTTATTTATA ATGAAATCAA CTAAAACTAT TTTTGCTATA AGTTCTATAA GGTGCATAAA     180

ACCCTTAAAT TCATCTAGTA GCTGTTCCCC CGAACAGGTT TATTTTAGTA AAAAAAAAAA     240

AC                                                                   242

(2) INFORMATION FOR SEQ ID NO:13:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TGAGATGTCC AGAAGATGTT ATTACCTGAA GAAGGGTGTG AAGGCTGGAC AATCATGGAT      60

TTTTCTGATC AATTGTGCTT TAGGAAATTA TTGACAGTTT TGCACAGGTT CTTGAAAACG     120

TTATTTATAA TGAAATCAAC TAAAACTATT TTTGCTATAA GTTCTATAAG GTGCATAAAA     180

CCCTTAAATT CATCTAGTAG CTGTTCCCCT GAACAGGTTT ATTTTAGTAA AAACAAAAA      240

CAAAACGAAA AAAAAAAAAA AAACGGAAAA AAAATCAAAG ATTTTTATCA AATATNNNAA     300

AAAAAAAAA                                                            309

(2) INFORMATION FOR SEQ ID NO:14:

(i) SEQUENCE CHARACTERISTICS:
        (A) LENGTH: 296 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:14:

TGAGATGTAC AGAAAGGTGT TCTTACATGA AGAAGGGTGT GAAGGCTGAA CAATCATGGA      60

TTTTTCTGAT CAATTGTGCT TTAGGAAATT ATTGACAGTT TTGCACAGGT TCTTGAAAAC     120

GTTATTTATA ATGAAATCAA CTAAAACTAT TTTTGCTATA AGTTCTATAA GGTGCATAAA     180

ACCCTTAAAT TCATCTAGTA GCTGTTCCCC CGAACAGGTT TATTTTAGTA AAAAAAAAAA     240

AGCAAAAAAC AAAAACAAAA GATTTTTATC AAATGTTATG ATGCAAAAAA AAAAAA         296
```